United States Patent [19]

Vandewalle et al.

[11] Patent Number: 5,162,335

[45] Date of Patent: Nov. 10, 1992

[54] DI- AND TETRAHYDROISOQUINOLINE DERIVATIVES

[75] Inventors: Maurits E. A. Vandewalle; Johan T. A. Van der Eycken, both of Gent, Belgium; Ineke van Wijngaarden, Weesp, Netherlands; Roelof van Hes, Weesp, Netherlands; Antonius Hulkenberg, Weesp, Netherlands; Christophorus M. J. F. Keet, Weesp, Netherlands

[73] Assignee: Duphar International Research B.V., Weesp, Netherlands

[21] Appl. No.: 480,755

[22] Filed: Nov. 27, 1989

Related U.S. Application Data

[63] Continuation of Ser. No. 123,326, Nov. 20, 1987, abandoned, Continuation-in-part of Ser. No. 50,425, May 18, 1987, abandoned.

[30] Foreign Application Priority Data

May 21, 1986 [NL] Netherlands ................. 8601279

[51] Int. Cl.$^5$ .................. A61K 31/335; A61K 31/47; C07D 405/00; C07D 471/04; C07D 221/04; C07D 471/06
[52] U.S. Cl. ...................... 514/291; 514/290; 514/294; 514/307; 514/309; 546/4; 546/5; 546/6; 546/10; 546/23; 546/62; 546/65; 546/79; 546/90; 546/93; 546/94; 546/95; 546/98; 546/99; 546/100; 546/101; 546/110; 546/111; 546/139; 546/141; 546/146; 546/147; 546/148; 546/150; 544/60; 544/126; 544/361; 540/542; 540/544; 540/553; 540/575; 540/599

[58] Field of Search ............ 546/4, 5, 6, 10, 23, 546/140, 90, 141, 65, 62, 79, 90, 93, 94, 95, 98, 99, 100, 101, 110, 111, 139, 141, 146, 147, 148, 150; 544/60, 126, 361; 540/542, 544, 599, 553, 575; 514/290, 291, 294, 307, 309

[56] References Cited

U.S. PATENT DOCUMENTS

| B 571,638 | 3/1976 | Yonan | 546/5 |
| 1,437,802 | 12/1922 | Hartmann et al. | 546/5 |
| 3,597,431 | 8/1971 | Coppola et al. | 546/5 |
| 3,629,265 | 12/1971 | Grethe et al. | 546/5 |

FOREIGN PATENT DOCUMENTS 1215656 12/1970 United Kingdom.

OTHER PUBLICATIONS

Mollov and Venkov, Eine neue Methode zur Synthese von 2-Acyl-1-aryl-1,2,3,4-tetrahydroisochinolinen, Synthesis, vol. 1, pp. 62–63, 1970.

Saxena, A. K. et al., Compounds Acting on the CNS: Part XXI-Synthesis of 2-Substituted 1,3,4,6,11,11α-Hexahydro-2 (H)pyrazino [1,2-b-]-isoquinoline & Corresponding 8,9-Dimethoxy- & 6-Phenyl-8,9-dimethoxy Analogs, Ind. J. of Chem. vol. 13, pp. 230–237. (1980).

Primary Examiner—Johann Richter
Attorney, Agent, or Firm—Finnegan, Henderson, Farabow, Garrett & Dunner

[57] ABSTRACT

The invention relates to new di- and tetrahydroisoquinoline derivatives having interesting cytostatic properties, to the preparation of the said new compounds, and to compositions comprising such a compound as a cytostatically active substance.

6 Claims, No Drawings

DI- AND TETRAHYDROISOQUINOLINE DERIVATIVES

This is a continuation of application Ser. No. 123,326, filed Nov. 20, 1987 now abandoned, which is a continuation-in-part application of Ser. No. 07/050,425, filed May 18, 1987, now abandoned.

The invention relates to a group of new isoquinoline derivatives, to the preparation thereof, and to pharmaceutical compositions comprising at least one of the said compounds as the active substance.

It was found that isoquinoline derivatives of the general formula (I)

wherein:

R, $R_1$, $R_2$ and $R_{13}$ independently of each other represent hydrogen, halogen, trifluoromethyl, $R+R_1$ or $R_2+R_{13}$ represent an aromatic or hetero-aromatic group having 5 or 6 ring atoms, or $R_1+R_2$ constitute a saturated or unsaturated carbocyclic ring or heterocyclic ring with 5-7 ring atoms which heterocyclic ring comprises 1-3 hetero atoms of the group N, O or S and may be substituted with alkyl having 1-4 carbon atoms, halogen or a double-bond oxygen atom or sulphur atom;

$R_3$ is hydrogen, hydroxymethyl, alkoxy or alkanoyloxy having 1-4 carbon atoms, hydroxy or hydroxy which is derivatised with a sugar radical the 4,6-hydroxy groups of which may be acetalised with an -ylidene group;

$R_4$ is hydrogen or a group of the formula $$+C)_{\overline{n}}X-R_{12},$$

wherein $R_{11}$ is hydrogen or methyl or both groups $R_{11}$ together represent a double bonded oxygen atom, n is 1 or 2, X is O, S, $CH_2$, NH or $NR_{16}$ wherein $R_{16}$ is alkyl having 1-4 C atoms, $R_{12}$ is hydrogen, alkyl having 1-4 C atoms, tetrahydropyranyl, alkanoyl having 1-4 C-atoms, or carbamoyl optionally substituted with 1 or 2 alkyl groups having 1-4 C-atoms, or X-$R_{12}$ is hydrogen or a 5-7 membered ring wherein X is nitrogen, which ring may contain O or S as a second hetero atom, or a group >NH or >$NR_{16}$;

$R_5$ is hydrogen, hydroxy, alkanoyl or alkyl having 1-4 C-atoms, or a group of the formula Ia (Ia)

wherein the symbols have the above and below indicated meanings, or the group $$-\underset{\underset{S}{\|}}{C}-S-CH_3,$$

or $R_4+R_5$ together represent a group of the formula $$+C)_{\overline{n}}X-Z-$$

with Z linked to the nitrogen atom, wherein $R_{11}$, X and n have above mentioned meanings, and Z is a group $$-\underset{\underset{O}{\|}}{C}-, -\underset{\underset{S}{\|}}{C}-, -S-, -CH_2-, -\underset{\underset{\downarrow}{|}}{\overset{|}{P}}-, -\underset{\underset{Cl}{|}}{\overset{Cl}{\underset{|}{Pt}}}- \text{ or } -\underset{\underset{CF_3}{|}}{\overset{|}{C}}-;$$

$R_6$ is hydrogen or $R_5+R_6$ together constitute a double bond;

$R_7$ and $R_9$, independently of each other, are hydrogen or alkoxy having 1-2 C-atoms;

$R_8$ is hydrogen, alkoxy or alkanoyloxy having 1-2 C-atoms or, hydroxy; or $R_7+R_8$ or $R_8+R_9$ together constitute the methylenedioxy group or ethylenedioxy group;

$R_{10}$ is hydrogen or methoxy; and $R_{14}$ is hydrogen or methyl, or $R_3+R_{14}$ together represent a bond, have very good cytostatic properties.

When in formula (I) one or more optically active centers are present, both the separate enantiomers, diastereomers and mixtures thereof belong to the invention.

Both the individual cis- and trans-isomers and mixtures thereof also belong to the invention.

The invention also relates to the acid addition salts and to prodrugs of the compounds of formula (I). Prodrugs are to be understood to mean compounds which are inactive in themselves and which after administration are converted in the body into an active compound of formula (I).

Suitable acids with which the compounds of formula (I) to be considered for that purpose may form pharmaceutically acceptable acid addition salts are, for example, hydrochloric acid, sulphuric acid, phosphoric acid, nitric acid, and organic acids, for example, citric acid, fumaric acid, maleic acid tartaric acid, acetic acid, benzoic acid, p-toluene sulphonic acid, methane sulphonic acid and naphthalene sulphonic acid.

The compounds according to the invention, their acid addition salts, and prodrugs can be processed by means of standard techniques to compositions such as pills, tablets, coated tablets, capsules, powders, injection liquids, and the like, while using auxiliary substances suitable for this purpose, for example, solid and liquid carrier materials.

The new compounds according to the invention can be obtained according to the following methods A and-/or B and/or C, dependent on the meaning of the symbols.

METHOD A

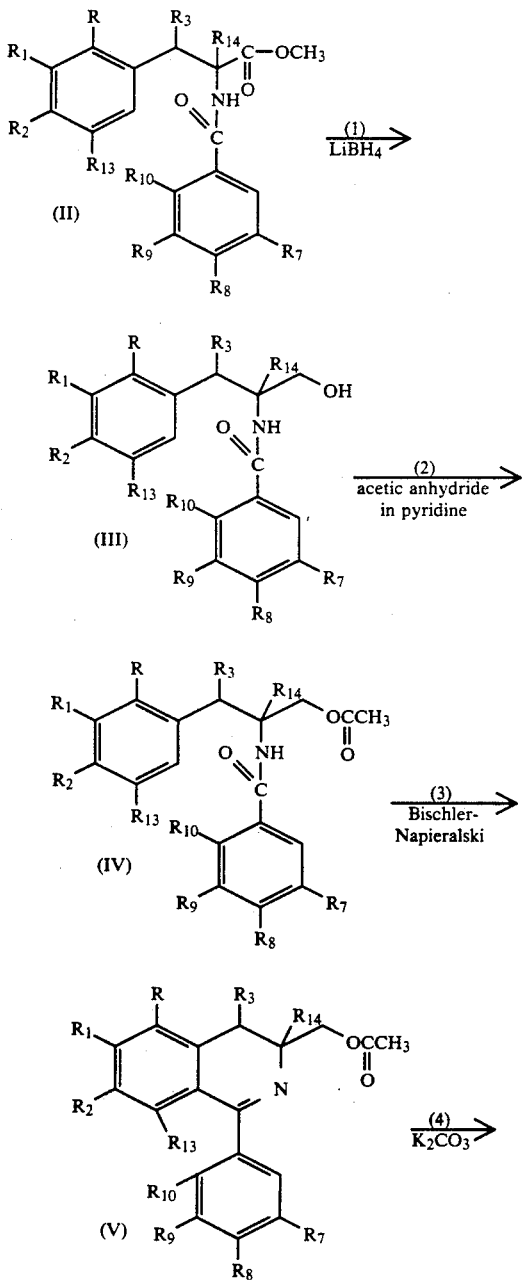

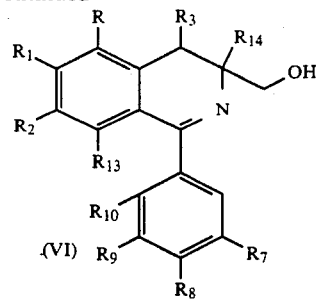

Starting compounds II are partly known compounds (for example, the compound II wherein $R=H$, $R_1+R_2=-O-CH_2-O-$, $R_3=H$, $R_7=R_8=R_9=OCH_3$ and $R_{10}=R_{13}=R_{14}=H$) and, in so far as they are new, they may be prepared in the same manner as the known compound.

Reaction steps (1)–(4) are carried out in circumstances which are usual for this type of reaction.

Final products VI according to the invention, i.e. the compounds of formula (I), wherein $R_5+R_6$ form a double bond, can be converted in a manner known per se into compounds of formula I, wherein $R_5$ and $R_6$ have the remaining meanings mentioned above by first hydrogenating the double bond, for example, with $AlCl_3$ and $LiAlH_4$ (or by a catalytic reduction of a salt of V), and optionally then introducing a substituent $R_5$.

METHOD B

Compounds of formula (I), wherein $R_1$ and $R_2$ are hydroxy, alkoxy, or an oxygen-containing heterocyclic group may also be obtained as follows:

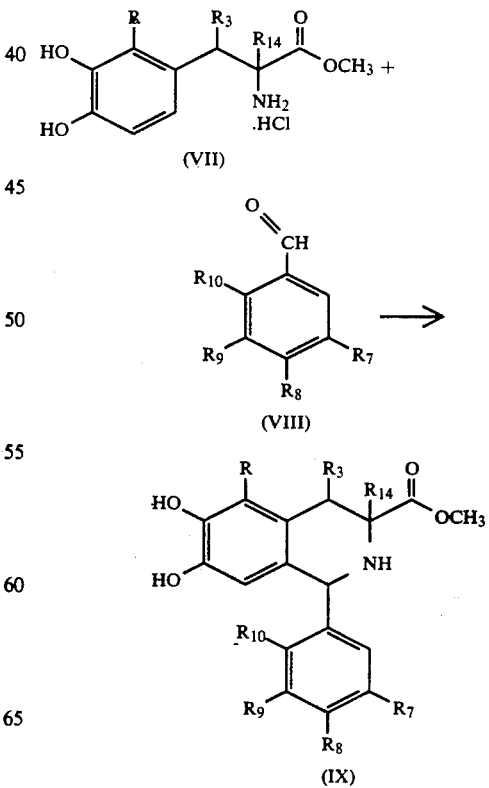

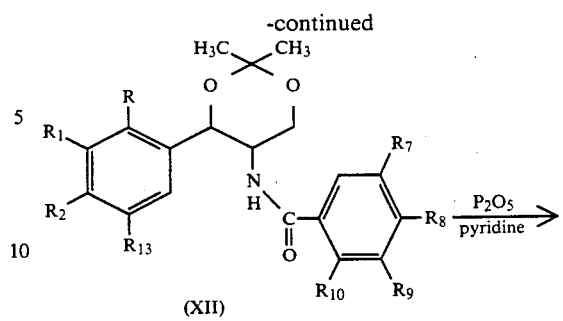

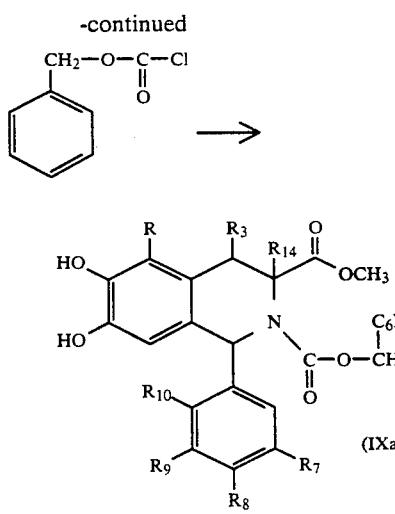

(IXa)

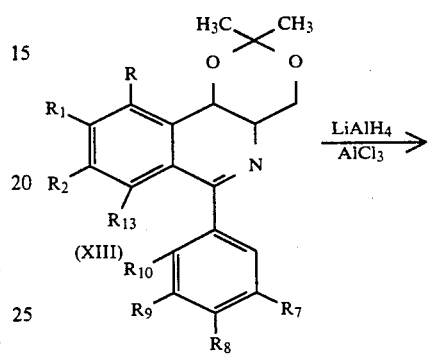

(XII)

Compounds VII are known or can be obtained in manner analogous to that of the known compounds (for example, $R=R_3=R_{14}=H$ is the methyl ester of L- or D-dopa). When IX is to be converted into compounds according to the invention, wherein $R_1$ and/or $R_2$ constitute(s) an alkoxy group, or $R_1+R_2$ constitute a heterocyclic ring, then the nitrogen atom in IX must first be protected, for example, by means of the tertiary butoxycarbonyl group or the benzyloxycarbonyl group by converting IX with, for example, benzyloxycarbonyl chloride. As the last reaction steps after introducing the desired substituents $R_1$ and/or $R_2$, the protective benzyloxycarbonyl group may be removed and the ester moiety can be converted into a group $CH_2OH$ as in reaction step (1) of method A, after which said alcohol group may optionally be further converted.

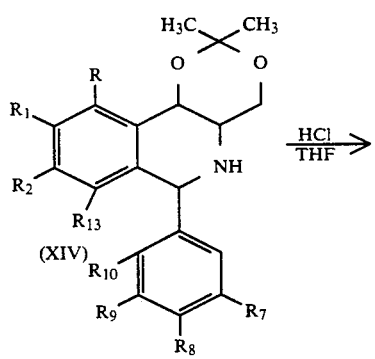

(XIII)

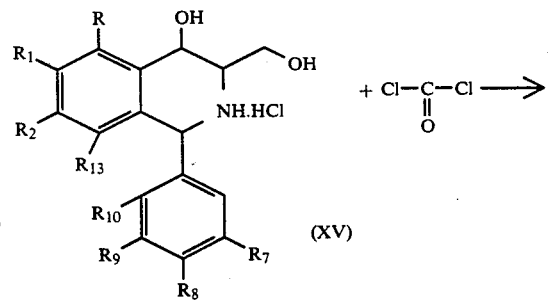

(XIV)

METHOD C

The compounds of formula I, wherein $R_3$ has a meaning other than hydrogen, can be obtained as follows

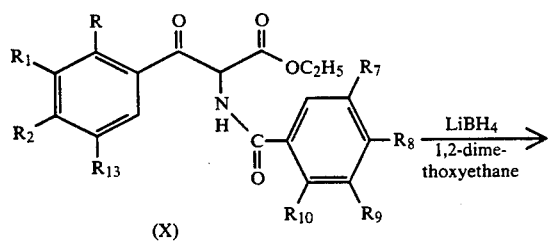

(X)

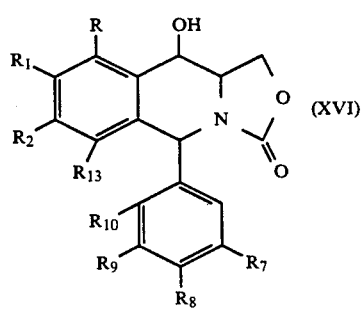

(XV)

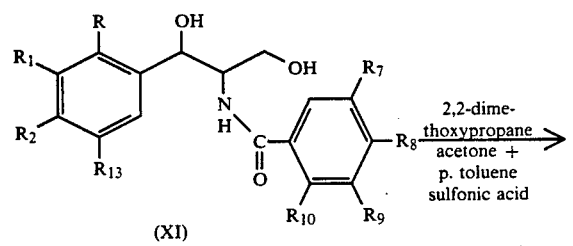

(XI)

(XVI)

The conversion of compounds XI with 2,2-dimethoxypropane serves to protect the hydroxy groups.

The ring closure of compounds XII with $P_2O_5$ in pyridine is known from Tetrahedron 6 (1959), p. 16 and 16 (1961), p. 63. The double bond at the N-atom of the compounds XIII thus obtained may be hydrogenated, if desired, in the manner described in method A, giving compound XIV.

As the last reaction step of the synthesis, the protective group is removed by means of hydrochloric acid in tetrahydrofuran. As in method A, the alcohol group $-CH_2-OH$ may be converted, if desired, into other groups $-CH_2-X-R_{12}$, for example, by reaction with phosgene into a compound XVI.

Intermediates XIV can also be obtained by reacting compound XVII and VIII in a slightly acidic alcoholic medium:

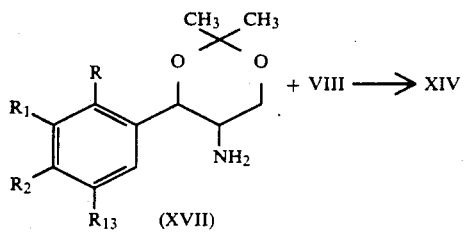

Compounds XVII are prepared according to methods known from Tetrahedron Letters 25, (1984), 5723.

The antitumor activity of the compounds according to the invention was tested in two in vitro tests.

1. HUMAN CELL LINE CYTOTOXICITY

A number of representative compounds of the group according to the invention is tested for cytotoxicity in at least five of the following human tumor cell lines: bladder T24, melanoma IGR37, breast MCF7, osteosarcoma A204, colon WIDR, HT29 and SW116 (P. P. Dendy and B. T. Hill, Human Tumour Drug, Sensitivity testing in vitro, Academic Press, 1983; H. B. Lamberts et al. Oncology 40, (1983), pp. 301–304; A. A. van der Huizen, Aziridinyl cyclophosphazenes, synthesis, structure and cytostatic activity, thesis (1984), Groningen).

PROCEDURE

Cells in a quantity of $10^5$ cells/ml of medium are provided on 24-well cluster plates. After incubation for 24 hours at 37° C. in an atmosphere of air with 5% $CO_2$, a suspension of the compound to be tested in 0.5% CMC/saline solution is added until a final concentration of 15 µg/ml.

Adriamycine is used as the positive control compound. After incubation for 72 hours in the presence of the compound to be tested, the cell layers are washed with a phosphate-buffered saline solution and the cells are coloured with crystal violet. The cell growth inhibition is estimated with reference to the coloured cells and is expressed as follows.

```
4 approximately 100% cell growth inhibition
3 approximately  75% cell growth inhibition
2 approximately  50% cell growth inhibition
1 approximately  25% cell growth inhibition
0 no cell growth inhibition.
```

2. CLONOGENIC ASSAY WITH HUMAN CELL LINES

A number of compounds according to the invention has been tested in the so-called clonogenic test (R. Ludwig et al, Cancer Chemother. Pharmacol. 12, (1984), pp. 135–141; W. I. Schaefer and K. Friend, Cancer Letters, 1, (1976), pp. 259–262; P. P. Dendy and B. T. Hill, Human Tumour Drug, Sensitivity testing in vitro, Academic Press, 1983). The following human cell lines are used: breast MCF7 and HTB26, colon WIDR and HTB38, lung HTB53, melanoma HTB66, and uterus HTB114.

As comparative substances are used cisplatinum, 5-fluorouracil, daunomycine, bleomycine and adriamycine.

PROCEDURE

Each cell line is provided in a quantity of approximately $10^2-10^5$ cells/dish and incubated at 37° C. in an atmosphere of air with 5% $CO_2$. During providing the cells or after a pre-incubation period of one night, the compound to be tested is added as a solution or suspension in 0.5% CMC/saline solution in a dose range with a maximum concentration of 15 µg/ml.

The duration of the treatment is approximately three times the cell cycle. The cells are then fixed, coloured and evaluated for the presence of the colonies. The formation of colonies is expressed in the number of colonies which is present on the treated dishes as a perecentage of the number of colonies which is present on control dishes.

In Tables A-D below the activity as determined in test method I is recorded of a number of compounds I according to the invention.

TABLE A

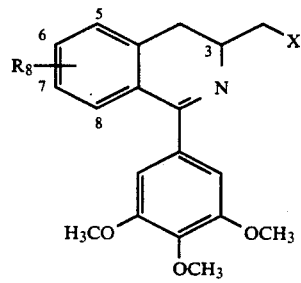

| Ex. no. | $R_B$ | X | melt. p. (°C.) | cytotoxicity acc. to meth. 1 | 3-D/L |
|---|---|---|---|---|---|
| 1 | 6,7-O—$CH_2$—O— | OH | 153 | 2-4 | DL |
| 2 | 6,7-O—$CH_2$—$CH_2$—O— | OH | 185 | 4-4 | DL |

TABLE A-continued

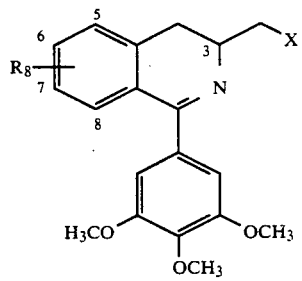

| Ex. no. | $R_B$ | X | melt. p. (°C.) | cytotoxicity acc. to meth. 1 | 3-D/L |
|---|---|---|---|---|---|
| 3 | 6,7-O—CH$_2$—O— | OTHP* | 122 | 0–3 | DL |
| 4 | 6-Cl | OH | 146 | 2–4 | DL |
| 5 | 6-Cl | —OCOCH$_3$ | 111 | 1–4 | DL |
| 6 | 5,6-CH=CH—CH=CH— | OH | 147 | 2–4 | DL |
| 7 | 6,7-O—CH$_2$—CH$_2$—O | OH | 147 | 4–4 | D |
| 8 | 6,7-O—CH$_2$—O— | H | 140 | 2–4 | DL |
| 9 | 5,6-HC=CH—CH=CH— | OH | 151 | — | L |

*OTHP = 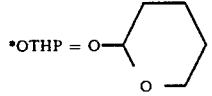

TABLE B

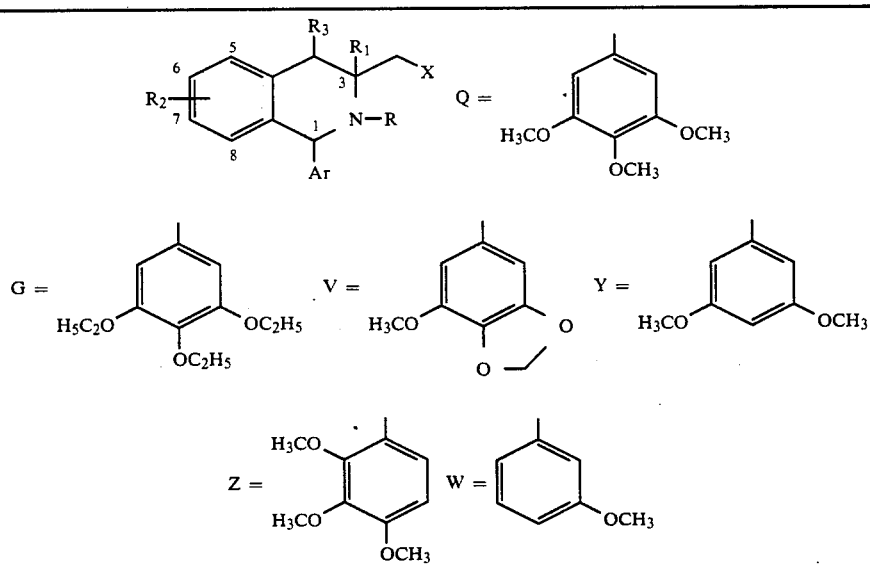

| Ex. no. | $R_2$ | R | $R_3$ | $R_1$ | Ar | X | melt. p. °C. | cytotox. acc. to meth. 1 | 1,3-cis/ trans | 3-D/L |
|---|---|---|---|---|---|---|---|---|---|---|
| 10 | 6,7-O—C—O | H | H | H | Q | OH | 170 | 1–4 | cis | DL |
| 11 | 6,7-O—C—O | H | H | H | Q | OH | 78 | 0–3 | trans | DL |
| 12 | 6,7-O—C—O | CH$_3$ | H | H | Q | OH | 148 | 0–4 | cis | DL |
| 13 | 6,7-O—C—C—O | H | H | H | Q | OH | 165 | 1–4 | cis | DL |
| 14 | 6,7-O—C—O | H | H | H | Q | O‖OC—CH$_3$ | 120 | 0–3 | trans | DL |
| 15 | 6,7-O—C—O | H | OH | H | Q | OH | 194 | 1–4 | cis* | DL |
| 16 | 6,7-O—C—O | H | H- | H | Q | O‖OC—CH$_3$ | 120 | 2–4 | cis | DL |
| 17 | 6,7-O—C—O | C—CH$_3$ ‖ O | H | H | Q | O‖OC—CH$_3$ | 197 | 3–4 | cis | DL |

TABLE B-continued

| | | | | | | | | | | |
|---|---|---|---|---|---|---|---|---|---|---|
| 18 | 6,7-O—C—C—C | H | H | H | Q | OH | 140 | 2-4 | cis | DL |
| 19 | 6,7-O—C—C—O | H | H | H | Q | OH | 174 | 2-4 | cis | L |
| 20 | 6,7-O—C—C—O | H | H | H | Q | OH | 177 | 2-4 | cis | D |
| 21 | 6-Cl | H | H | H | Q | OH | 104 | 0-4 | cis | DL |
| 22 | 6,7-O—C—C—O | H | H | H | Y | OH | 185 | 0-4 | cis | L |
| 23 | 5,6-C=C—C=C | H | H | H | Q | OH | 161 | 2-4 | cis | DL |
| 24 | 6,7-O—C—C—O | H | H | H | Q | OH | 150 | 2-4 | trans | D |
| 25 | 6,7-O—C—C—O | H | H | CH₃ | Q | OH | 204 | 0-2 | trans | DL |
| 26 | 7,8-C=C—C=C | H | H | H | Q | OH | 158 | 2-4 | cis | DL |
| 27 | 6,7-O—C—C—O | H | H | H | Q | O‖OC—C | 134 | 4-4 | cis | D |
| 28 | 6,7-O—C—C—O | O‖C—CH₃ | H | H | Q | O‖OC—C | 164 | 4-4 | cis | D |
| 29 | 6,7-O—C—C—O | H | H | H | G | OH | 144 | 4-4 | cis | D |
| 30 | 6,7-O—C—C—O | H | H | H | Q | O‖O—C—C(C)(C)—C | 125 | 2-4 | cis | D |
| 31 | 6,7-O—C—C—O | H | H | H | Z | OH | 74 | 0-4 | cis | D |
| 32 | 6,7-O—C—C—C—O | H | H | H | Q | OH | 176 | 4-4 | cis | D |
| 33 | 6,7-O—C—C—O | H | H | H | Y | OH | 178 | 4-4 | cis | D |
| 34 | 6,7-O—C—C—O | H | H | H | D | OH | 70 | 2-4 | cis | D |
| 35 | 6,7-O—C—C—O | H | H | H | Q | NH₂ | 112 | 2-4 | cis | D |
| 36 | 6,7-O—C—C—O | H | H | H | E | OH | 133 | 4-4 | cis | D |
| 37 | 6,7-O—C—C—O | H | H | H | W | OH | 144 | 4-4 | cis | D |
| 38 | 6,7-O—C—C—O | H | H | H | V | OH | 160 | 4-4 | cis | D |
| 39 | 6,7-O—C—C—O | H | OH | H | Q | OH | 186 | 4-4 | cis* | DL |
| 40 | 6,7-O—C—C—O | CH₃ | H | H | Q | OH | 161 | 2-4 | cis | D |
| 41 | 6,7-O—C—O | H | OH | H | Q | OH | 225 | 4-4 | cis* | DL |
| 42 | 6,7-O—C—C—O | H | OH | H | Q | OH | 190 | 4-4 | cis** | DL |
| 43 | 6,7-O—C—O | H | OH | H | Q | OH | 183 | 2-4 | cis** | DL |
| 44 | 6,7-O—C—O | H | H | H | Q | OH | 219 | 4-4 | cis¹⁾ | DL |
| 45 | 6,7-O—C—O | H | OH | H | C | OH | 194 | — | cis** | DL |
| 46 | 6,7-O—C—O | H | H | H | Q | OH | 161 | 2-4 | cis | D |
| 47 | 6,7-O—C—C—O | (PtCl₂)½ | H | H | Q | OH | 165 | 2-4 | cis | D |
| 48 | 6,7-O—C—O | (PtCl₂)½ | H | H | Q | OH | 243 | 2-4 | cis | DL |
| 49 | 6,7-O—C—O | H | H | H | Q | H | 128 | 3-4 | cis | DL |
| 50 | 6,7-O—C—O | H | H | H | Q | H | 139 | 0-3 | trans | DL |
| 51 | 5,6-C=C—C=C | H | H | H | Q | OH | 144 | — | cis | D |
| 52 | 6,7-O—C—C—O | H | R₁-R₃ a bond | | Q | OH | — | 4-4 | — | 1-DL |
| 53 | 5,6-C=C—C=C | H | H | H | Q | OH | 146 | — | cis | L |

*1,4-cis HCl-salt
** 1,4-cis
¹⁾CH₃SO₃H-salt

TABLE C

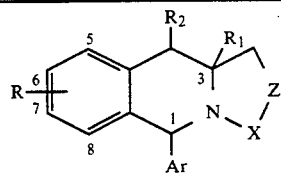

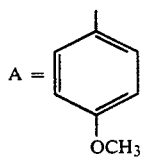 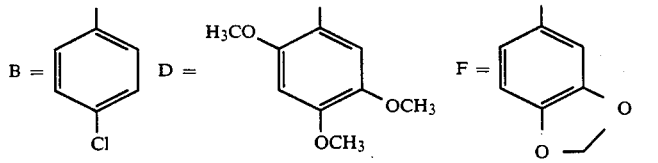

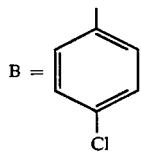 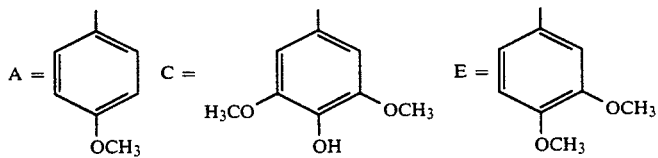

| Ex. no. | R | R₂ | R₁ | Z—X | melt. p. °C. | Ar | cytotox. acc. to meth. 1 | 1,3-cis/ trans | 3-D/L |
|---|---|---|---|---|---|---|---|---|---|
| 54 | 6,7-O—C—O | H | H | O—C=O | 229 | Q | 2-4 | cis | DL |
| 55 | 6,7-O—C—O | H | H | O—S→O¹⁾ | 231 | Q | 2-4 | cis | DL |
| 56 | 6,7-O—C—O | H | H | O—S→O¹⁾ | 213 | Q | 0-4 | cis | DL |
| 57 | 6,7-O—C—O | H | H | O—C=S | 209 | Q | 2-4 | cis | DL |
| 58 | 6,7-O—C—C—O | H | H | O—S→O¹⁾ | 276 | Q | 4-4 | cis | DL |
| 59 | 6,7-O—C—C—O | H | H | O—S→O¹⁾ | 256 | Q | 1-4 | cis | DL |
| 60 | 6,7-O—C—C—O | H | H | O—C=S | 241 | Q | 1-4 | cis | DL |
| 61 | 6,7-O—C—C—O | H | H | O—C=O | 240 | Q | 2-4 | cis | DL |
| 62 | 6,7-O—C—O | H | H | O—S→O | 154 | A | 3-4 | cis | DL |
| 63 | 6,7-O—C—O | OH | H | O—C=O | 226 | Q | 4-4 | cis²⁾ | DL |
| 64 | 6,7-O—C—O | H | H | O—S→O | 170 | B | 2-4 | cis | DL |
| 65 | 6-Cl | H | H | O—C=O | 155 | Q | 3-4 | cis | DL |
| 66 | 6,7-O—C—C—C | H | H | O—C=O | 196 | Q | 2-4 | cis | DL |
| 67 | 6,7-O—C—O | H | H | CH₃ \| N—C=O | 211 | Q | 2-4 | cis | DL |
| 68 | 6,7-O—C—O | H | H | O—CH₂ | 188 | Q | 2-4 | cis | DL |
| 69 | 6,7-O—C—O | H | H | O—C=O | 95 | C | 4-4 | cis | DL |
| 70 | 6,7-O—C—O | H | H | CH₃ \| N—S→O | 215 | Q | 4-4 | cis | DL |
| 71 | 6,7-O—C—O | H | H | O—C=O | 186 | Q | 4-4 | trans | DL |
| 72 | 6,7-O—C—O | H | H | O—C=S | 208 | Q | 4-4 | trans | DL |
| 73 | 6,7-O—C—O | H | H | O—S→O¹⁾ | 202 | Q | 3-4 | trans | DL |
| 74 | 6,7-O—C—O | H | H | O—S→O¹⁾ | 179 | Q | 4-4 | trans | DL |
| 75 | 6,7-O—C—O | H | H | O—CH₂ | 172 | Q | 2-4 | trans | DL |
| 76 | 6,7-O—C—O | H | H | NH—C=O | 265 | Q | 3-4 | cis | DL |
| 77 | 6,7-O—C—O | H | H | NH—C=S | 211 | Q | 0-2 | cis | DL |
| 78 | 6,7-O—C—C—O | H | H | O—C=O | 183 | Q | 4-4 | cis | L |
| 79 | 6,7-O—C—C—O | H | H | O—C=O | 190 | Q | 4-4 | cis | D |

TABLE C-continued

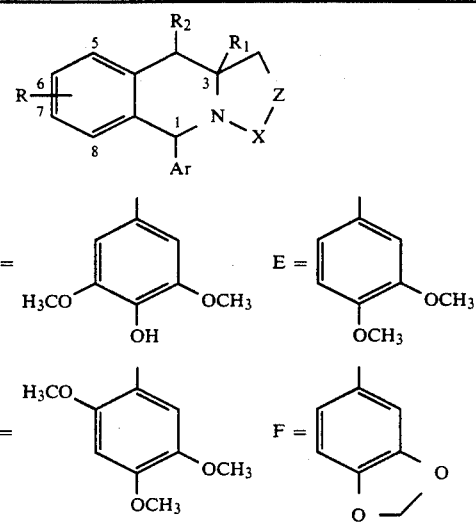

A = 4-methoxyphenyl
B = 4-chlorophenyl
C = 3,5-dimethoxy-4-hydroxyphenyl
D = 3,4,5-trimethoxyphenyl
E = 3,4-dimethoxyphenyl
F = 3,4-methylenedioxyphenyl (ethylidenedioxy)

| Ex. no. | R | R₂ | R₁ | Z—X | melt. p. °C. | Ar | cytotox. acc. to meth. 1 | 1,3-cis/ trans | 3-D/L |
|---|---|---|---|---|---|---|---|---|---|
| 80 | 6,7-O—C—C—O | H | H | O—C=O | 274 | D | 4-4 | cis | L |
| 81 | 5,6-C=C—C=C | H | H | O—C=O | 198 | Q | 4-4 | cis | DL |
| 82 | 7,8-C=C—C=C | H | H | O—C=O | 238 | Q | 4-4 | cis | DL |
| 83 | 6,7-O—C—C—O | H | H | O—C=O | 213 | E | 0-2 | cis | L |
| 84 | 6,7-O—C—C—O | H | H | O—C=O | 205 | F | 2-4 | cis | L |
| 85 | 6,7-O—C—C—O | H | CH₃ | O—C=O | 176 | Q | 4-4 | trans | L |
| 86 | 6,7-O—C—C—O | H | H | O—C=O | 90 | G | 2-4 | cis | D |
| 87 | H | | | O—C=O | 165 | Q | 2-4 | cis | DL |
| 88 | 6,7-O—C—C—O | H | H | O—C=O | 139 | Y | 4-4 | cis | L |
| 89 | 6,7-O—C—O | H | H | O—P(=O)—Cl (O) | 177 | Q | 4-4 | cis | DL |
| 90 | 6,7-O—C—O | H | H | O—P(Cl)(O)(O) | 220 | Q | 4-4 | cis | D |
| 91 | 6,7-O—C—C—O | H | H | O—C=O | — | Z | 2-4 | cis | D |
| 92 | 6,7-O—C—C—O | H | H | O—S→O¹⁾ | 220 | Q | 4-4 | cis | D |
| 93 | 6,7-O—C—C—O | H | H | O—S→O¹⁾ | 212 | Q | 4-4 | cis | D |
| 94 | 6,7-O—C—C—O | H | H | O—S→O¹⁾ | gum | Q | 2-4 | cis | L |
| 95 | 6,7-O—C—C—O | H | H | O—S→O¹⁾ | 213 | Q | 2-4 | cis | L |
| 96 | 5,6-C=C—C=C | H | H | O—S→O¹⁾ | 196 | Q | 2-4 | cis | DL |
| 97 | 5,6-C=C—C=C | H | H | O—S→O¹⁾ | 196 | Q | 2-4 | cis | DL |
| 98 | 6,7-O—C—C—O | H | H | H₂N—PtCl₂ | 257 | Q | 2-4 | cis | D |
| 99 | 6,7-O—C—C—C—O | H | H | O—C=O | 217 | Q | 4-4 | cis | D |
| 100 | 6,7-O—C—C—O | H | H | O—C=O | 98 | Y | 4-4 | cis | D |
| 101 | 6,7-O—C—C—O | OH | H | O—C=O | 255 | Q | 4-4 | cis³⁾ | DL |
| 102 | 6,7-O—C—C—O | H | H | O—C=S | 239 | Q | 4-4 | cis | D |
| 103 | 6,7-O—C—O | OH | H | O—C=O | 268 | Q | 4-4 | cis³⁾ | DL |
| 104 | 6,7-O—C—C—O | H | H | O—C=O | 189 | E | — | cis | D |
| 105 | 6,7-O—C—C—O | H | H | O—C=O | 232 | V | — | cis | D |
| 106 | 5,6-C=C—C=C | H | H | O—C=O | 173 | Q | — | cis | D |

TABLE C-continued

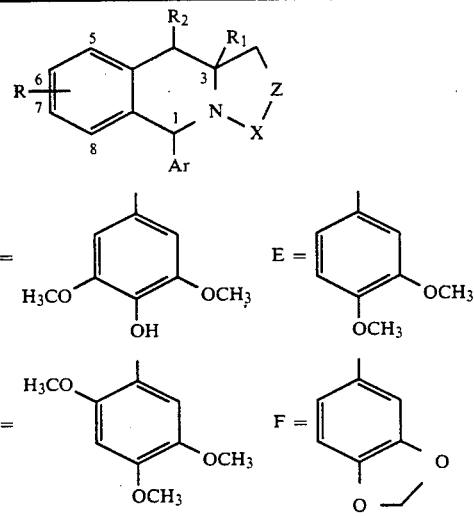

| Ex. no. | R | $R_2$ | $R_1$ | Z—X | melt. p. °C. | Ar | cytotox. acc. to meth. 1 | 1,3-cis/ trans | 3-D/L |
|---|---|---|---|---|---|---|---|---|---|
| 107 | 5,6-C=C—C=C | H | H | O—C=O | 173 | Q | — | cis | L |

[1] pair of stereoisomers
[2] 1,4-trans
[3] 1,4-cis

TABLE D

| Ex. no. | R | Ar | X | $R_5$ | cytotox. acc. to meth. 1 | melt. p. °C. | 1,3-cis/ trans | 3-D/L |
|---|---|---|---|---|---|---|---|---|
| 108 | 6,7-O—C—C—O | Q | COOCH$_3$ | H | 0-2 | 172 | cis | L |
| 109 | 6,7-O—C—C—O | Q | COOCH$_3$ | H | 4-4 | 179 | cis | D |
| 110 | 6,7-O—C—C—O | Q | CONH$_2$ | H | 4-4 | 155 | cis | D |
| 111 | 6,7-O—C—O | Q | H | H | 3-4 | 102 | cis | DL |
| 112 | 6,7-O—C—C—O | G | COOCH$_3$ | H | 2-4 | 123 | cis | D |
| 113 | 6,7-O—C—C—O | G | CONH$_2$ | H | 4-4 | 85 | cis | D |
| 114 | 6,7-O—C—C—O | Q | CONHC—C—CH$_3$ | —HC=O | 4-4 | 96 | cis | D |

The compounds of example nos. 20, 23, 55, 70, 79-82 and 110 (more particularly the D-enantiomers thereof) are of particular interest since they are very cytotoxic as measured according to the method of test 1, and give ID$_{75}$ values in the clonogenic assay (test 2) of less than 1 μg/ml.

EXAMPLE I a. Ring Closure According to Method A:

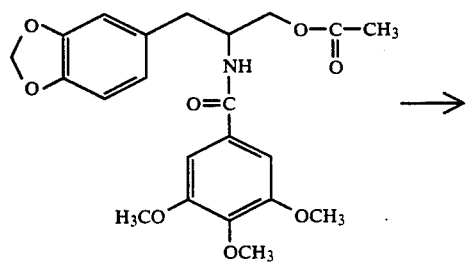 →

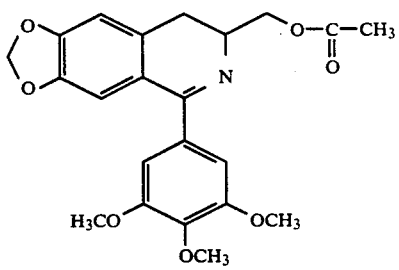

2 g of the amide (4.64 mmol) are dissolved in 40 ml of dichloromethane and treated at room temperature with 2.8 g of PCl$_5$ (13.4 mmol). After stirring for 30 minutes, 1.2 g of AlCl$_3$ (9 mmol) is added under an atmosphere of argon. The mixture is stirred overnight at 20° C. After making the mixture basic with an NaOH solution, one extraction with ethyl acetate is performed. The organic phase is washed with NaCl until neutral, and dried with MgSO$_4$. After evaporation, 1.64 g of the dihydroisoquinoline is obtained as a yellow oil. The original aqueous phase and the formed precipitate are extracted overnight with ethyl acetate and in an identical manner 130 mg of the dihydroisoquinoline are obtained therefrom. Yield is 1.77 g (92%).

b. Conversion of the Acetoxy Group into the Hydroxy Group 6.5 g (15.74 mmol) of the acetate according to a. are dissolved in 240 ml of methanol and treated with 6.5 g of dried $K_2CO_3$. After approximately 2 hours the methanol is evaporated and the residue is taken up in $CH_2Cl_2$. $K_2CO_3$ is filtered off for the greater part and the filtrate is washed with water. The aqueous phase is extracted several times with $CH_2Cl_2$ and the combined fractions are dried on $Na_2SO_4$. 0.5 ml of triethylamine per 100 ml of $CH_2Cl_2$ are added to prevent the formation of insoluble HCl salts. After filtering off and evaporation, a yellow oil (6 g) is obtained. After crystallisation from ether/$CH_2Cl_2$, 4.85 g (83%) of a crystalline product are obtained having a melting-point of 153° C.

c. Preparation of the Tetrahydroisoquinoline

A solution of 467 mg (3.5 mmol) of $AlCl_3$ in 10 ml of THF is added dropwise at room temperature to a suspension of 400 mg (10.5 mmol) of $LiAlH_4$ in 20 ml of tetrahydrofuran (THF), as a result of which $AlH_3$ is formed. After 15 minutes the solution is cooled to $-30°$ C. and a solution of 2.5 g (6.74 mmol) of the dihydroisoquinoline according to b. in 100 ml of THF is added dropwise in 15 minutes. The reaction mixture is then slowly heated to room temperature. After 1.5 hours an NaOH solution in $H_2O$ is added until everything has dissolved. The organic phase is separated, and the aqueous phase is washed once with ethyl acetate/ether and four times with ether. The combined organic phases are washed with saline solution and dried with $Na_2SO_4$. After evaporation the tetrahydroisoquinoline (melting-point 160° C.) is obtained as a light-yellow powder (2.45 g, i.e. (2.45 g, i.e. 97%).

d. Ring Closure with Phosgene 100 mg (0.268 mmol) of the amino compound to be obtained according to c. are dissolved in 3 ml of dichloromethane containing 0.3 ml of triethylamine, and treated with phosgene. After working up in the usual manner, 95 mg (i.e. 89%) of the light-yellow carbamate (compound 54, Table C) are obtained as a light-yellow powder (melting-point 229° C.).

In an analogous manner compounds wherein X is C=S or S→O were obtained by treating the corresponding amino compounds with thiophosgene, thionyl chloride or phosphoroxychloride, respectively.

EXAMPLE II a. Preparation of Compound IX from VII.

2.6 g (1.1 equivalents) of sodium bicarbonate are added to a suspension of 7.14 g of L-Dopa methyl ester hydrochloride in 25 ml of acetic acid and the whole is stirred for 5 minutes. 5.6 g of 3,4,5-trimethoxybenzaldehyde are then added and the mixture is stirred overnight at room temperature. The reaction mixture is then poured out on 100 ml of 5% sodium bicarbonate and the whole is made neutral by the addition of solid sodium bicarbonate. Four extractions with 200 ml of dichloromethane are then carried out. The organic layers are washed neutral with $3 \times 150$ ml of water, dried with $MgSO_4$, filtered and evaporated. Yield is 10.5 g of compound IX ($R=R_3=R_{10}=R_{14}=H$; $R_7=R_8=R_9=OCH_3$).

b. Protection of the N-H Group in IX 780 mg of the compound IX to be obtained according to a. are dissolved in 10 ml of dichloromethane and 0.28 ml of triethylamine are then added. A solution of 0.29 ml of benzyloxycarbonyl chloride in 5 ml of dichloromethane is added dropwise at 0° C. and the mixture is stirred overnight at room temperature, and is then poured out in $H_2O/CH_2Cl_2$. The layers are separated, the aqueous layer is washed twice with 50 ml of $CH_2Cl_2$, and the collected organic fractions are washed with $2 \times 50$ ml of $H_2O$, dried with $MgSO_4$, filtered and evaporated. Yield is 1.08 g of compound IXa, in which the hydrogen atom at nitrogen is replaced by the benzyloxycarbonyl group.

c. Ring Closure with Dibromomethane

A mixture of 1.08 g of the compound IXa., 0.82 g of potassium carbonate, 0.33 ml of dibromomethane, and 10 ml of acetone is boiled for 24 hours. After the addition of another 0.5 g of potassium carbonate and 0.5 ml of dibromomethane, the mixture is boiled again for 24 hours. The acetone is evaporated and the residue is divided over 50 ml of water and 100 ml of dichloromethane. The layers are separated and the aqueous layer is extracted two times with 50 ml of $CH_2Cl_2$. The collected organic layer is washed twice with 75 ml of water, dried with $MgSO_4$, filtered and evaporated. Yield 1.1 g of yellow oil. This oil is purified by means of a wet silica gel column with ether as the eluent. Yield is 700 mg of a white powder of the compound IXa., in which the two hydroxy groups have been converted into the methylene dioxy group.

d. Removal of the Protective Group from the N-atom

The product (700 mg) to be obtained according to c. is dissolved in 15 ml of methanol and a quantity of 10% of Pd/C is added. The mixture is reduced at room temperature for 4 hours under 1 atmosphere of $H_2$. The reaction mixture is filtered over hyflo and the filtrate is evaporated. Yield is 510 mg of a yellow solid. After purification over a wet silica gel column with ethyl acetate as the eluent, 410 mg of a white solid are obtained (compound according to c., from which the benzyloxycarbonyl group has been removed).

The methoxycarbonyl group in this compound is converted in a manner known per se into the hydroxymethyl group by means of $LiBH_4$.

EXAMPLE III a. 150 mg of compound XIV ($R_1+R_2=O$—$CH_2$—$O$—; $R=R_{10}=R_{13}=H$; $R_7=R_8=R_9=OCH_3$) are dissolved in 8 ml of THF and 6 ml of 1N HCl. After stirring at room temperature for 20 hours, the mixture is evaporated to dryness and taken up in isopropanol. After crystallisation, 135 mg of the HCl-salt of compound XV (melting-point 194° C., decomposition) are obtained (compound 15, Table B).

This compound is treated with phosgene in the manner described in EXAMPLE 1d. In this manner, 40 mg of the compound XVI (light-yellow substance, melting-point 226° C., decomposition) are obtained (compound 63, Table C).

EXAMPLE IV 232 mg (0.6 mmol) of compound no. 20 is dissolved in 8 ml of water containing 288 mg (3,0 mmol) of methane sulfonic acid. While stirring a solution of 125 mg (0,3 mmol) of potassium tetrachoroplatinate (II) in 2.5 ml of water is added. The mixture is stirred for one hour, filtered off and washed with cold water. The yield is 205 mg of compound no. 47 (melting point 165° C.; decomposition).

EXAMPLE V 128 mg (0,33 mmol) of the compound which is obtained after reduction of the amide group X of compound no. 110 with LiAlH4 (i.e. $X = —CH_2NH_2$), is dissolved in 8 ml of 0.2N HCl. While stirring a solution of 137 mg (0.33 mmol) of potassium tetrachoroplatinate (II) in 1.5 ml of $H_2O$ is added. The reaction mixture is stirred for 90 min., filtered off and washed with cold water. In this maner 150 mg of compound no. 98 having a melting point of 257° C. (decomposition) is obtained.

We claim:

1. Di- and tetrahydroisoquinoline derivatives of the formula (I):

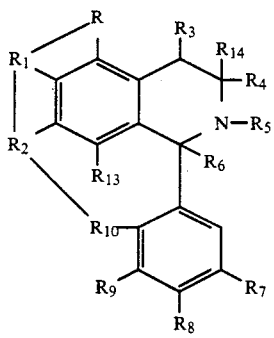

wherein:
- R, $R_1$, $R_2$, and $R_{13}$ are independently selected from the group consisting of hydrogen, halogen and trifluoromethyl; or
- $R + R_1$ together with the carbon atoms to which they are bound represent a ring selected form the group consisting of: an aromatic carbocyclic ring, ethylenedioxide, methylenedioxide and propylenedioxide; or
- $R_1 + R_2$ together with the carbon atoms to which they are bound represent a ring selected from the group consisting of: a saturated carbocyclic ring, ethylenedioxide, methylenedioxide and propylenedioxide; or
- $R_2 + R_{13}$ together with the carbon atoms to which they are bound represent a ring selected from the group consisting of: an aromatic carbocyclic ring, ethylenedioxide, methylenedioxide and propylenedioxide;
- $R_3$ is selected from the group consisting of: hydrogen, hydroxymethyl, alkoxy or alkanoyloxy having 1-4 carbon atoms, and hydroxy;
- $R_4$ is selected from the group consisting of: methyl, aminomethyl, $-CH_2-OR_{12}$, an alkanoyloxy group of 2 to 6 C-atoms, an alkoxycarbonyl group with 1 to 3 C-atoms in the alkoxy moiety, and $-CO-N(R_{11})_2$, wherein $R_{11}$ is selected from the group consisting of hydrogen and alkyl having 1 to 3 carbon atoms; and
- $R_{12}$ is selected from the group consisting of hydrogen and tetrahydropyran-2-yl;
- $R_5$ is selected from the group consisting of hydrogen, hydroxy, alkanoyl or alkyl having 1-4 C-atoms, and the group

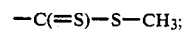

- $R_6$ is hydrogen;
- $R_5 + R_6$ together constitute a double bond;
- $R_7$ and $R_9$, independently of each other, are hydrogen or alkoxy having 1-2 C-atoms;
- $R_8$ is selected from the group consisting of: hydrogen, alkoxy or alkanoyloxy having 1-2 C-atoms, and hydroxy;
- $R_7 + R_8$ or $R_8 + R_9$ together constitute a methylenedioxy group or ethylenedioxy group;
- $R_{10}$ is hydrogen or methoxy;
- $R_{14}$ is hydrogen or methyl; and
- $R_3 + R_{14}$ together constitute a double bond; and acid addition salts and prodrugs thereof.

2. A compound as claimed in claim 1, characterized in that it is the D-enantiomer.

3. A compound according to claim 1 having the formula

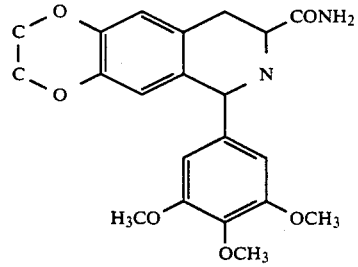

4. A compound according to claim 1 having the formula

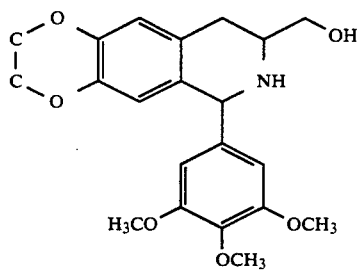

5. A compound according to claim 1 having the formula

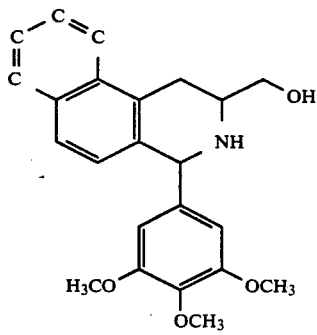

6. A cytostatic composition comprising as the active ingredient an effective amount of at least one cytostatically active compound as claimed in claim 1, and a pharmaceutically acceptable carrier.

* * * * *